US008884752B2

(12) United States Patent
Tai et al.

(10) Patent No.: US 8,884,752 B2
(45) Date of Patent: Nov. 11, 2014

(54) MEDICATION USAGE MONITORING AND REMINDING DEVICE AND METHOD

(75) Inventors: Chih-Cheng Tai, Sunnyvale, CA (US); Lucas J. Myslinski, Sunnyvale, CA (US); Chyh-Yih Chang, Xinzhuang (TW); Shih-Ming Tseng, Santa Clara, CA (US); Shih-Hsiang Tseng, Santa Clara, CA (US)

(73) Assignee: Tai and Tseng Investments LLC, Campbell, CA (US)

( * ) Notice: Subject to any disclaimer, the term of this patent is extended or adjusted under 35 U.S.C. 154(b) by 1357 days.

(21) Appl. No.: 12/510,133

(22) Filed: Jul. 27, 2009

(65) Prior Publication Data

US 2010/0283601 A1    Nov. 11, 2010

Related U.S. Application Data

(60) Provisional application No. 61/215,894, filed on May 11, 2009.

(51) Int. Cl.
| G08B 1/08 | (2006.01) |
| G06Q 50/24 | (2012.01) |
| G08B 21/24 | (2006.01) |

(52) U.S. Cl.
CPC ............ *G08B 21/24* (2013.01); *G06Q 50/24* (2013.01)
USPC ............ 340/539.12; 340/539.1; 340/573.1; 713/161; 434/236; 434/247; 434/322; 463/1; 463/16; 463/43; 463/44

(58) Field of Classification Search
USPC .............. 340/539.12, 539.1, 573.1; 713/161; 434/236, 247, 322; 463/1, 16, 43, 44
See application file for complete search history.

(56) References Cited

U.S. PATENT DOCUMENTS

| 5,042,685 | A |  | 8/1991 | Moulding, Jr. et al. |
| 5,758,095 | A |  | 5/1998 | Albaum et al. |
| 7,122,005 | B2 |  | 10/2006 | Shusterman |
| 8,092,224 | B2 | * | 1/2012 | Walker et al. ................ 434/236 |
| 2003/0086338 | A1 | * | 5/2003 | Sastry et al. .................... 368/10 |
| 2006/0285441 | A1 | * | 12/2006 | Walker et al. ................... 368/10 |
| 2007/0016443 | A1 | * | 1/2007 | Wachman et al. ............... 705/2 |
| 2007/0186923 | A1 |  | 8/2007 | Poutiatine et al. |
| 2008/0256445 | A1 | * | 10/2008 | Olch et al. ................... 715/700 |
| 2009/0134181 | A1 | * | 5/2009 | Wachman et al. ............... 221/8 |
| 2010/0164716 | A1 |  | 7/2010 | Estevez et al. |

* cited by examiner

*Primary Examiner* — Daryl Pope
(74) *Attorney, Agent, or Firm* — Haverstock & Owens LLP

(57) ABSTRACT

The medication usage monitoring and reminding device and method enables a user to easily monitor usage of medications by weighing the medications using a weighing component, a processing component and an I/O component. Additionally, the device is able to remind a user regarding the medications if the medication has not been timely taken. The device is also able to obtain information regarding medications such as possible conflicts, updates and other information. The device is able to be used for food/drink information or dietary information.

20 Claims, 6 Drawing Sheets

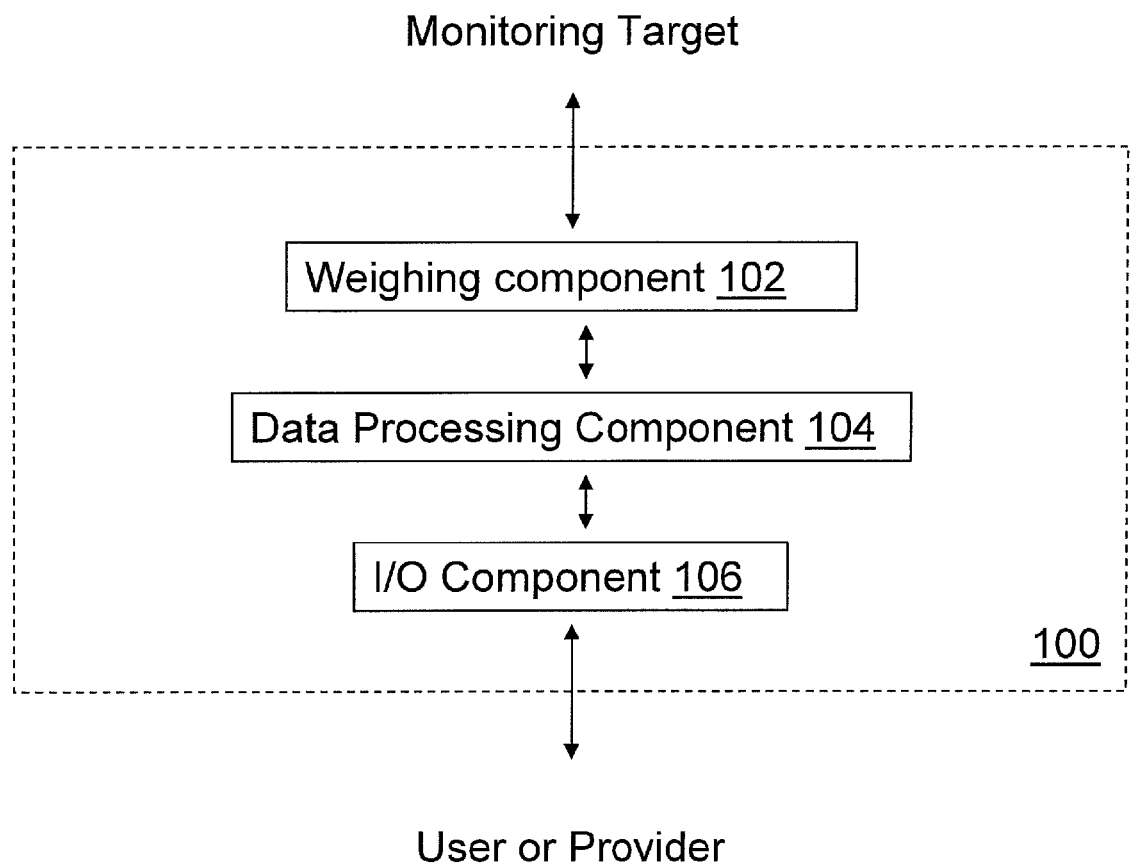

| Weighing Component 102 | Data Processing Component 104 | |
|---|---|---|
| Scale 200 | Processor 220 | Storage 224 |
|  | Memory 222 | Comp. System 226 |
|  | Database(s) 228 |  |
| I/O Component 106 | | | |
| Keyboard 250 | Touchpad 252 | Mouse 254 | Barcode Reader 256 |
| RFID Reader 258 | Display 260 | Imaging 262 | Touchscreen 264 |
| Computer 266 | Dial/Lever/Knob/ Button 268 | Voice Recog. 270 | Wireless 272 |
| Wi-Fi 274 | Network 276 | Blood Pressure 278 | Insulin 280 |
| Thermometer 282 | Alert/Alarm 284 | GPS 286 | Speaker(s) 288 |
| Radio 290 | Television 292 | Security 294 | Indicator(s) 296 |

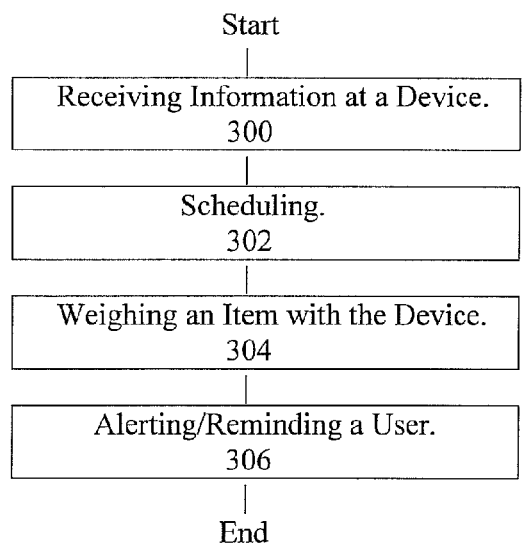

| Text | Medication Information | Network Data | Menus |
|---|---|---|---|
| Images | Tracking Information | Contact Information | Stored Information |
| Videos | Reminder information | Nutrition Information | Diet Plans |
| Audio | Calculations / Calculated Information | Synchronization Information | Additional Information |
| Links | Input Data | Recipes | |

MEDICATION USAGE MONITORING AND REMINDING DEVICE AND METHOD

CROSS-REFERENCE TO RELATED APPLICATIONS

This application claims the priority under 35 U.S.C. §119 (e) of U.S. Provisional Patent Application Ser. No. 61/215,894, filed May 11, 2009, and entitled "MEDICATION USAGE MONITORING AND REMINDING DEVICE AND METHOD," which is hereby incorporated by reference in its entirety for all purposes.

FIELD OF THE INVENTION

The present invention relates to the field of medication usage monitoring and reminding. More particularly, the present invention relates to the field of medication usage monitoring and reminding using a weighing device to determine the time, amount, and/or types of medicine taken.

BACKGROUND OF THE INVENTION

People take many different medications per day. Initially, these people would merely do their best to ensure they did not forget to take some medication. However, even with their best efforts, pills were not always timely taken. Different pill tracking systems have been developed, but they have significant flaws. For example, daily pill containers store pills for each day of the week but still require diligence on the part of the user. People are also constantly attempting to "watch what they eat," but fail to do so effectively.

SUMMARY OF THE INVENTION

The medication usage monitoring and reminding device and method enables a user to easily monitor usage of medications by weighing the medications using a weighing component, a processing component and an I/O component. Additionally, the device is able to remind a user regarding the medications if the medication has not been timely taken. The device is also able to obtain information regarding medications such as possible conflicts, updates and other information. The device is able to be used for food/drink information or dietary information.

In one aspect, a device for monitoring medication usage comprises a medication removal recognition component configured for recognizing removal of a medication and generating medication removal recognition data, an input/output (I/O) component coupled to the medication removal recognition component, the I/O component configured for communicating I/O data, a data processing component configured for processing the medication removal recognition data and the I/O data including determining a weight change data and a medication reminding component coupled to the data processing component, the reminding component configured for reminding a user to take the medication.

The medication removal recognition component is selected from the group consisting of a mechanical weighing device, an electronic weighing device, a two-sides balance and a piezoelectric load cell.

The data processing component is configured for computing the weight change data by subtracting a non-initial weight from an initial weight to obtain a result and dividing the result by an individual medication weight. The data processing component is configured for computing the weight change data by subtracting a current weight from an immediately preceding weight. The data processing component is configured for recording at least one of a weight date, the weight change data and a time of weight change data. The data processing component is configured for converting at least one of the weight date, the weight change data and the time of weight change data into medication usage information. The medication usage information comprises at least one of a time of a medication taken, a dosage of a medication taken and a type of a medication taken.

The I/O component comprises a display device configured for displaying the medication usage information. The I/O component is coupled to a second device for communicating at least one of a weight information, a stock information, a medication information and the medication usage information. The I/O component is coupled to a medication supply system, wherein the medication supply system is configured for receiving a notification of a quantity of the medication taken. The I/O component is coupled to an information system of a medical service provider, wherein the medical service provider is configured for performing at least one of monitoring, commenting, recording and replying regarding medication information received through a network. The I/O component is synchronized with a personal information system, wherein the personal information system provides an alert if a medication is not taken within a pre-designated time.

The personal information system is selected from the group consisting of a mobile device, a pager, a cell phone, a blackberry, a laptop and a personal digital assistant. The I/O component is coupled to an information system including a medical database, wherein the medical database is configured for comparing a medication information and generating an alert if there is an incompatible medication. The I/O component is coupled to a physical condition monitoring device configured for monitoring a physical condition before, after, or while a medication is taken.

The physical condition monitoring device is configured for monitoring at least one of a heart rate, a medication concentration in blood stream, a chemical fluid concentration and a physical fluid concentration in a body. The medication reminding component reminds a user at a computed reminder time based on a time of previous medication consumption, a medication dosage and a weight of the user. The I/O component is able to be selected from the group consisting of a screen/display, a keyboard, a mouse, a touchscreen, a touchpad, a light emitting diode, a speaker, a radio, a television, a computer, a dial, a lever, a knob, a button, a voice-recognition implementation, a wireless implementation, a wi-fi implementation, a network coupling, a bar code reader/scanner, an RFID reader/scanner, an image recognition component, a blood pressure monitor, an insulin monitor, a thermometer, and any combination thereof.

In another aspect, a system for monitoring medication usage implemented on a device comprises a medication removal recognition module configured for recognizing removal of a medication and generating medication removal recognition data, a Radio Frequency Identification (RFID) reader module operatively coupled to the medication removal recognition module, the RFID reader component configured for receiving RFID data, a data processing module configured for processing medication removal recognition data and the RFID data including determining a weight difference between a stored weight and a current weight and storing the weight difference, a network module configured for communicating network information between the data processing component and an external device, a reminding module coupled to the data processing module, the reminding module configured for reminding a user to take the medication based on a schedule and a display coupled to the data processing module, the display configured for displaying medication information.

In yet another aspect, a method of monitoring medication usage comprises receiving medication information at an Input/Output (I/O) component, weighing a medication with a device and including computing a weight difference between a first weighing and a second weighing, scheduling a schedule on the device, reminding a user to take a medication based on the schedule and communicating with an external device over a network, wherein medication information is communicated.

BRIEF DESCRIPTION OF THE DRAWINGS

FIG. 1 illustrates a block diagram of a medication monitoring and reminding device according to some embodiments.

FIG. 2 illustrates a block diagram of a device according to some embodiments.

FIG. 3 illustrates a flowchart of a method of using the device according to some embodiments.

DETAILED DESCRIPTION OF THE PREFERRED EMBODIMENT

Figure 4:
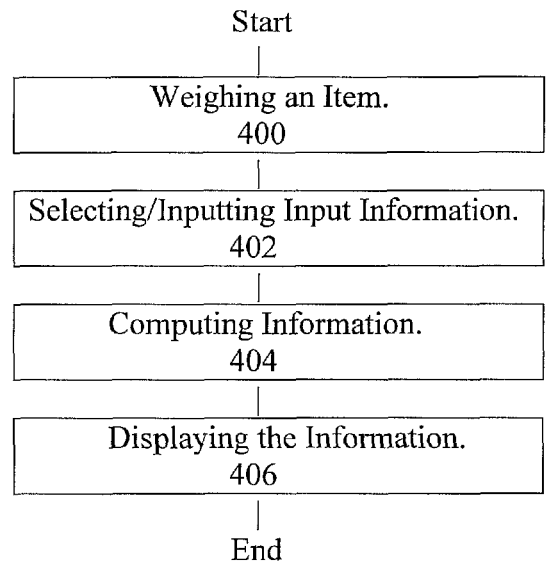
FIG. 4 illustrates a flowchart of a method of using the device for dietary purposes according to some embodiments.

To help ensure users do not miss a medication, a medication monitoring and reminding device is able to be used. The medication monitoring and reminding device is able to notify the user, the medicine suppliers, and the health professionals about the time when the user should take a pill, user's (or a group of users') past medicine usage information, and when to supply more medicine.

FIG. 1 illustrates a block diagram of a medication monitoring and reminding device 100 according to some embodiments. The medication monitoring and reminding device 100 includes a weighing component 102, a data processing component 104 and an Input/Output (I/O) component 106. The weighing component 102 is configured for weighing an item and/or determining a weight difference. The data processing component 104 is configured for processing data, such as the data received from the weighing component 102 and/or the I/O component 106. The I/O component 106 is coupled to the weighing component 102 and/or the data processing component 104 for providing information such as medicine usage information. The medication monitoring and reminding device 100 is able to include fewer or additional components as well.

The weighing component 102 is able to be any kind of weighing implementation or device such as a scale. The scale is able to be any type of scale including, but not limited to, a mechanical scale, an electronic scale, a two-side balance, a load cell or any other type of weighing device. The weighing component 102 is able to weigh any object including but not limited to, medication, food, drink, pet food, pet medication, vitamins, items (e.g. condoms, contact lenses and coins) and other objects. The medication is able to be in any form such as pills, powder, liquigels, liquids, gas and other forms. The medication is able to be any medication, for example, birth control pills. In some embodiments, there are multiple weighing components 102 for weighing separate items. In some embodiments, the weighing component 102 includes separate zones, each zone configured for weighing a separate item. In some embodiments, the weighing component 102 is able to weigh and remind for multiple items (e.g. medications) at the same time.

In some embodiments, using the weighing component 102 includes weighing an item such as a pill which has a consistent weight, in other words, each pill has approximately the same weight. The pill is able to be a solid, liquid-gel, pill containing liquid or any other type of pill. In some embodiments, using the weighing component 102 includes weighing an initial amount of liquid, gas or solid, and subtracting to calculate the amount of liquid, gas or solid taken. In some embodiments, using the weighing component 102 includes weighing an initial amount of a gas (e.g. asthma medication), and subtracting to calculate the amount of gas taken. In some embodiments, a full, partially full and/or an empty container such as a bottle is weighed to be used in calculations. In some embodiments, a full container with pills is weighed, then a pill is removed and the partially full container is weighed and the weight difference is determined. The weight difference is used to determine the weight of am individual pill. In some embodiments, the number of pills is then input by a user or is determined by the device 100. In some embodiments, instead of weighing to determine an initial weight, weight information is stored and is able to be selected by the user. For example, Viagra typically comes in a standard container with 30 pills, so that weight information is able to be selected by a user. In some embodiments, even if the container is not standard, the information is able to be selected. For example, a user is able to select a type of container and the number of pills from options (e.g. options of 10, 20, 30 pills).

The following is another example of weighing a medication. A user puts a full bottle on the device 100, and in some embodiments, waits for a brief period of time (e.g. 3 seconds). The device 100 prompts the user to input the number of pills in the bottle. The user then inputs the number of pills in the bottle (which is able to be found on the bottle). The user then removes 1 pill from the bottle while still on the device 100. The device 100 detects the weight change. In some embodiments, device monitors the weight changed for a brief period of time (e.g. 3 seconds) to record the weight change. The process is repeated for the first 5 pills. The average weight of the 5 pills is calculated and used as the weight of 1 pill since pills may vary slightly in weight. After a certain number of pills are removed, the device 100 shows that the pill amount is low. If a user does not acquire the pills, the device 100 contacts a pharmacy automatically. This example eliminates the need for a user to weigh a pill for test weighing purposes, eliminates the need to weight an empty bottle and determines when the pill amount is low but not based on an exact amount. This example also uses the brief period of time to weigh to remove the potential of faulty weighings/readings.

In some embodiments, a pill is detected as removed when a weight difference is detected. For example, a previous weight is detected and/or stored and then a current weight is detected and the difference between the current weight and the previous weight is detected and/or stored.

Any weighing process is able to be implemented using the weighing component 102 in conjunction with the data processing component 104 to determine a weight difference.

As described above, the data processing component 104 is configured for processing data. In some embodiments, the data processing component 104 is configured to receive data from the weighing component 102 and/or the I/O component 106. In some embodiments, the data processing component 104 is configured for receiving medication information from an existing database, and comparing the medical information with an existing database with information such as pre-stored drug information. In some embodiments, the data processing component 104 is configured for processing information entered such as keyed-in information through the I/O component 106. The data processing component 104 is able to process any kind of information. In some embodiments, the data processing component 104 is able to determine information about an item by taking known information and weighing information and performing a calculation. For example, if X-brand pills are known to weigh 100 mg (e.g. from a database), and there are 100 pills in a container, the container weight is able to be calculated by taking the total weighed amount and subtracting the known pill weight. Then, when the weight decreases, the device 100 is able to track that pills have been taken. Similarly, the container weight is able to be known too. Any methods of determining weight are possible.

In some embodiments, the data processing component 104 is able to record information such as weight, weight difference, time of medication taken, dosage taken, who has taken the medication and other information. The weight difference is able to be determined using any method. For example, in some embodiments, an initial weight (e.g. combined container and full number of pills) is stored, and then for each subsequent weighing, the difference between the initial weight and the subsequent weight is computed, and then that difference is divided by an individual serving of the medication (e.g. 1 pill) to determine the amount of medication taken. That number is then able to be compared with the previous amount of medication taken to determine if there has been a decrease and by how many. As another example, in some embodiments, each time a new weight is computed, that new weight is stored, and then the subsequent weight is compared with that stored weight to determine the difference and amount of medication taken. The information is able to be received from the weighing component 102, the I/O component 106, another component and/or calculated by the data processing component 104 or another component. The weight information is able to be calculated and converted into medicine information which is able to be stored as well. The data processing component 104 is also able to store a schedule for taking medications. The schedule is able to be input by a user through the I/O component 106, downloaded from a pharmacist, doctor or veterinarian, suggested by the device 100 based on past medication use records, suggested by a drug manufacturer and/or input/retrieved in another manner. The data processing component 104 is able to store any kind of information.

In some embodiments, the data processing component 104 includes a mechanism to perform simple calculations such as an adder. In some embodiments, the data processing component 104 includes a processor and/or a memory. In some embodiments, the data processing component 104 includes additional hardware such as additional storage (e.g. a hard drive). The data processing component 104 includes hardware, software, firmware or any combination thereof.

The I/O component 106 is able to be any kind of input receiving and/or output producing mechanism including but not limited to a screen/display such as an LCD or LEDs, a keyboard, a mouse, a touchscreen, a touchpad, a speaker, a radio, a television, a computer, a dial, a lever, a knob, a button or series of buttons, a voice-recognition implementation, a wireless implementation, a wi-fi implementation, a network coupling, a bar code reader/scanner, an RFID reader/scanner, an image recognition implementation, blood pressure monitor, insulin monitor, thermometer, moisture meter, any other I/O implementation or any combination thereof. The network coupling is able to allow any network capabilities such as over a cellular network, telephone network/landline, a LAN, WAN, MAN, the Internet and any other network and/or a combination thereof. The I/O component 106 includes hardware, software, firmware or any combination thereof.

The I/O component 106 is able to receive input from a user. The user is able to manually enter information such as name, date, sex, age, medication, dosage, frequency, medical information, medical allergies, allergies and other information. The I/O component 106 is able to link to other devices (e.g. a pharmacy computer) to receive information. The device 100 is able to automatically enter information through the use of the I/O component 106 such as a bar code scanner, RFID reader or an image recognition device which is able to retrieve desired information from an image.

The I/O component 106 is able to link to an external device such as a computer at a pharmacy, doctor's office, police or fire station, a dietician, a personal trainer, relative or friend's house, an advertiser, a store, a business, or any other external device, through a network or a direct link. The I/O component 106 is able to link to a pharmacy for stock monitoring such as for on-time delivery. The I/O component 106 is able to link to a physician device for time/dosage usage monitoring. The device 100 and/or the I/O component 106 is also able to link to or be a part of a personal device such as a mobile/cellular phone, personal digital assistant, personal computer, laptop, a pager, a gaming console, a baby monitor, a baby timing device, a Global Positioning System (GPS) or other device. The GPS is also able to track and send a reminder not to drive if the user has taken a medication that is able to inhibit driving abilities within a certain amount of time. The GPS is able to aid in locating a user of the device 100. The I/O component 106 is able to communicate with a vehicle to prevent the vehicle from turning on based on the medication and timing of taking the medication to avoid a potential accident. In some embodiments, the device 100 is able to be used to monitor alcohol consumption. For example, a user is able to input personal information such as weight and use the device 100 to calculate how much alcohol he has drunk in a certain duration, and then based on the information, determine his blood alcohol content level.

The I/O component 106 is able to link the device 100 to a database such as a medication database. The database is able to store any information including but not limited to a user's name, medication information such as weight information and calculations, contact information, medication conflict information and other information. The database is able to provide warnings of conflicting medication or inform a user of possible side effects such as chest pain after taking Viagra. The database is able to store information received from the I/O component 106. The database is able to be stored on the device 100 or on another device at a separate location. The database is able to receive updates including periodic updates. In some embodiments, the database keeps track of and stores daily, weekly, monthly and/or another time period usage. For example, if a user takes 1 pill Monday, 1 pill Tuesday, misses a pill Wednesday and takes a pill Thursday, that information is able to be recorded and utilized. Similarly, if a user takes two pills in the same day, that information is able to be recorded and possibly used to inform a medical professional.

The I/O component 106 is also able to link to an insurance company system for medication taking recording. The I/O component 106 is able to link to a relative's message device (e.g. a parent's mobile phone to remind the child to take medication). The I/O component 106 is able to link to a personal physical condition monitoring device which is able to alert the proper authorities such as the police, 9/11, a doctor, hospital and others.

The I/O component 106 is able to include an alerting/reminding mechanism which is able to alert a user if a medication is not taken on time. The alerting mechanism is able to be visual, audio, text, another sense, and/or any combination thereof. The alerting mechanism is able to provide reminders, for example, alerting a user that it is time to take a specific medication. The alerting mechanism is also able to alert a user to place the item on the device so that it is able to be weighed and monitored.

The I/O component 106 is able to receive and/or display information. The I/O component 106 is able to provide alert information as well. The I/O component 106 is able to display information such as directions, warnings, status of medicine usage, discount information received from a pharmacy about medicine on sale, prestored/wireless/Internet information and other information. For example, if a user receives information about refilling a medication, the user is able to respond via the I/O component 106. The user is able to send and receive questions and answers through the I/O component 106. The I/O component 106 is able to receive generic medication suggestions. The I/O component 106 is able to monitor blood pressure (e.g. monitoring blood pressure after medicine is taken). Other side effect monitoring is able to take place. The I/O component 106 is able to link to a medicine review forum. The I/O component 106 is able to record statistics such as when medicine is taken, response time, concentration in blood, heart rate and/or erection duration (e.g. after taking Viagra) as well as other statistics. A bar code is able to be preassigned by a pharmacy. The device 100 is able to recognize the content/ingredient/kind/amount of the bottle of pills when reading the bar code. The bar code information is able to include a type of drug, specific user's medical information stored in the device 100 and/or at a pharmacy and/or other information.

The device 100 is able to include any power source such as a battery, solar power, A/C power, wind power, fuel cell and other power sources.

In some embodiments, the device 100 is able to include fewer or more of the components described above. For example, there are able to be two weighing components and multiple I/O components such as a network coupling, a display and a keyboard.

In some embodiments, the device 100 is configured to assist disabled people. For example, for vision-impaired users, audio commands are able to be used to inform the user and for the user to communicate (e.g. voice input) with the device 100. Additionally, Braille inputs are able to be included as well, such as a Braille keyboard and/or display. For hearing-impaired users, visual interfaces are able to be used.

In some embodiments, where multiple users are utilizing the device 100, an identification verification is implemented. The identification verification is able to be implemented in hardware, software, firmware or any combination thereof. Any implementation of identification verification is possible. In some embodiments, a user is able to log in using a user-name and password for verification. In some embodiments, the device 100 displays a user's name when reminding the user to take a medication. In some embodiments, a different (e.g. unique) reminder is used for each user. For example, for 5 users, each user has a different alarm that is played to remind the user. In some embodiments, a technology such as RFID or a bar code is used to ensure the proper user is taking the medication. For example, an RFID tag is in a user's watch, bracelet or other object, and the device 100 is able to read the tag to ensure the medication and user match. The identification verification is able to facilitate communal use of the device 100, for example, at a nursing home or a hospital.

A feature of the device 100 includes security to ensure medications are not taken improperly. For example, a major concern involves abuse of prescription medications, for example, by children. The device 100 is able to sound an alarm if a medication is removed and not returned to the device 100 in a timely manner. The device 100 is also able to sound an alarm if the medication is returned with an improper amount of the medication removed. For example, if a user is expected to only take one pill per day, but it is recognized that many pills have been removed in a single day, the alarm is able to be sounded. In some embodiments, the alarm is able to be disabled by entering in a password or other implementation. In some embodiments, an alarm/alert is sent to a parent's device (e.g. mobile phone, work computer or other) to inform them immediately.

The device 100 is able to link with other medicine management systems. For example, personal medicine dispensers which automatically presort pills into separate components.

In some embodiments, the device 100 is able to weigh food/drink to determine caloric intake and other dietary information. In some embodiments, the device 100 is able to determine calories, fat, sodium, protein, carbohydrates, vitamins, minerals, allergy information and other information of the food/drink item. For example, the calories and other information in a specified food are known. After weighing the food, the calories for the amount of food are able to be computed and stored. In some embodiments, the device 100 includes and/or couples to a set of information such as a database that stores information for different foods.

In some embodiments, a user is able to input information for items not within the database such as via the I/O component 106. In some embodiments, the I/O component 106 includes selectable options for foods such as text and/or graphics and/or videos. For example, pictures of food items are displayed for a user to select. In some embodiments, a search implementation is able to be used to find an item such as a text search. The device 100 is able to store information in a variety of increments, such as per day/month/year. For example, before, during or after a user eats breakfast, the device is able to record the dietary information of the current moment and/or the cumulative information, and then use the information to inform him how many calories he has eaten that day. The device 100 is able to include a guide and/or menu such as an indication that a user has eaten 500 calories today so far and should eat 500 more, and display the foods left available for the user to eat today.

In some embodiments, the device 100 and/or the database is coupled to a user's kitchen/cupboard/refrigerator to know what items are available in the user's house. In some embodiments, the device 100 is able to convert information. For example, if data for a food item is in grams, the device 100 is able to convert the data into ounces. In another example, the I/O component 106 is able to take pictures of a Big Mac, search the Internet and find calories of a Big Mac and use that information accordingly.

In some embodiments, the device 100 is embedded in a table, countertop, refrigerator or another location. In some embodiments, the device 100 is embedded in or part of or all of a device such as a mobile phone, personal digital assistant, laptop or other device.

In some embodiments, the device 100 is able to take a picture and/or video of an item and recognize the item. The device 100 is able to then determine information about the item such as calories, sodium, protein, carbohydrates, vitamins, minerals, allergy information and other information (e.g. information found on food labels) per serving. The device 100 is able to provide a warning for allergy information. In some embodiments, the allergy warning is a generic warning simply informing a user of allergy contents, and in some embodiments, the allergy warning is specific to a user. In some embodiments, the device 100 includes a user interface for the user to verify the item and/or information regarding the information. For example, at a restaurant a user is able to take a picture of lunch, and the device 100 is able to determine the food/drink on the plate including quantity. Then, the device 100 is able to compute the food information. In some embodiments, restaurants are able to register and/or provide information to a system which the device 100 is able to communicate/link to.

For food/drink/other items with an identification mechanism such as RFID or a barcode, the food information is able to be contained in the identification mechanism and retrieved by the device 100. In some embodiments, the device 100 is able to take a picture of a label (e.g. food label), recognize the text of the image and convert it into usable information to be stored.

In some embodiments, the device 100 is able to be used as a shopping assistant. The device 100 is able to store a grocery list, check off an item when found, keep an ongoing price total, provide a price check for each item, keep a menu list, store food information from the foods on the lists (e.g. carbohydrates, proteins and other dietary information), recommend items (e.g. if a user likes chocolate cookies, he may want to buy chocolate ice cream too), advertising (e.g. you are purchasing tortilla chips, would you also like to purchase brand-X salsa?), present coupons, provide suggestions based on medical conditions (e.g. you are overweight, might I suggest diet soda) and perform other tasks. In some embodiments, a user is able to pay using the device 100 instead of going to a check out stand. The device 100 is also able to include a verification mechanism to verify the proper amount is paid for the items purchased.

In some embodiments, a system includes a device 100 and other devices such as a refrigerator/freezer and a food storage area. The system is able to maintain knowledge regarding a user's diet, menus, recipes, available food, needed food, medications, related-medical information, medical history and other information. The system is able to aid a user with medical and dietary needs.

In some embodiments, the device 100 is able to alert a user if he/she is about to eat a harmful item such as something too sugary for one with diabetes, something high in sodium for one with high blood pressure or an item containing an allergen for one allergic to that allergen.

In some embodiments, threshold(s) are able to be configured/set for each day/week/month/year and/or another desired time period. The threshold is able to be related to anything the user desires, for example, sodium, fat, cholesterol, sugar, alcohol, or anything else. The device 100 is able to indicate a relation to the threshold by any implementation. For example, if a user is monitoring sodium intake per week and is not close to the threshold, the device 100 is able to illuminate green, but when the sodium intake is approaching the threshold, the device 100 illuminates yellow, and when the sodium intake is over the threshold, the device 100 illuminates red. For a further example, if the device 100 is used to set/control a daily alcohol consumption limit for a specific user, the device 100 is able to supply or control the supply of the alcoholic drinks. The limits are able to be based on predetermined weight of the total alcohol supplied/consumed. For example, 50 ml (assuming 50 g) 40% alcohol contained wine A and 20 ml (assuming 20 g) 20% alcohol contained wine B would have total 24 g of alcohol. Thus, if the predetermined daily alcohol consumption limit is 20 g, the device will stop or make the corresponding/cooperating device stop supplying more alcoholic drinks (and/or provide an alert/warning) when total 20 g of alcohol drinks are supplied. However, if the predetermined daily alcohol consumption limit is 30 g, the device 100 is able to supply all alcohol drinks requested (50 ml wine A and 20 ml win B.) In some embodiments, the device 100 is able to further include an alcohol concentration sensor. The device 100 stops supplying alcohol (and/or provides an alert/warning) when the user's breath has an alcohol concentration higher than predetermined amount. On the other hand, if the user's breath has an alcohol concentration lower than predetermined amount, the device 100 is able to supply the alcoholic drinks as requested.

In some embodiments, the device 100 is able to be a fluid consumption monitoring device. A busy office worker often forgets to drink sufficient water when they are in the office. The device 100 is able to help to monitor and remind the office worker to drink sufficient water. For example, if the predetermined amount of water needed to be drunk is 1000 ml in the morning, the device 100 is able to automatically calculate and divide the 1000 ml water to be drunk into 250 ml for each hour. If the user does not drink the required amount of water before the device 100's suggested time, the device 100 is able to send a reminder to the user. Similarly, the device 100 is able to be applied to monitor the baby's milk consumption and mother's milk preservation and output.

In some embodiments, when a pill is taken on time, a green LED indicates an OK status; a yellow LED indicates a late status; and a red LED and/or an audible alarm and/or sending a signal to a physician and relatives indicates an overdose.

In some embodiments, the device 100 is able to communicate with or be synchronized with another device such as a user's mobile phone, pager, laptop and/or work computer. The device 100 is able to send a signal so that the synchronized device provides an alarm/alert/reminder. For example, if the device 100 is scheduled to remind a user at 7 pm to take medication, but the user is not at home to hear the reminder on the device 100, the device 100 is able to send the reminder to the user's mobile device which then reminds the user. In some embodiments, the device 100 initiates its alarm and if the alarm is not turned off in a time period, then the device 100 contacts a synchronized device or several synchronized devices in an order based on priority, for example, first a mobile device, then a work computer and then a relative's device. In some embodiments, the synchronization occurs and then all of the synchronized devices are able to remind the user without the device 100 contacting each one at a time. For example, at 6 pm, both the device 100 and the user's mobile device remind the user. The synchronization among the device 100 and other devices is also able to allow the other devices to modify including adding/deleting settings/information on the device 100 and/or retrieve information from the device 100. In some embodiments, the user is able to communicate with the device 100 using the synchronized or external device. For example, the user is able to turn off the reminder, push the reminder to a later time so that the user is reminded when he returns home or another affect the reminder in another way.

In some embodiments, the device 100 is able to weigh a person, baby, animal or other. In some embodiments, the device 100 is able to communicate and/or receive information from an external weighing device (e.g. a bathroom scale). The information received from the external weighing device will facilitate a user monitoring his/her diet. For example, if the user's weighs himself/herself weekly, the device 100 is able to record that information and/or chart it for the user to see. The device 100 is also able to perform additional calculations and analysis that shows when a user eats a diet of vegetables and fruits, X pounds were lost, but when the diet was mostly carbohydrates, Y pounds were lost. In some embodiments, the device 100 is able to communicate with an exercise device to receive exercise information. For example, the device 100 is able to record that a user worked out for 30 minutes, 3 days a week. In some embodiments, the device 100 is able to communicate with any device that is able to provide information usable by the user and/or the device 100. In some embodiments, the device 100 is able to generate charts, graphs and/or other data to inform the user of dietary/exercise information.

In some embodiments, the device 100 is able to be used for non-food or medication related items such as coins. For example, the device 100 is able to be used as a piggy bank with an alarm. After coins are added on the device 100, it is able to record the weight of the coins. If any coins are removed, the weight will change, and an alarm will sound thus protecting the coins. A user is able to disarm the alarm by entering a password or some other implementation. The device 100 is able to calculate the amount of money based on weight. In some embodiments, there are separate components, weighing components 102 or other features to allow coins to be weighed separately for the calculations. For example, a first compartment is configured for pennies, a second compartment is configured for nickels, and so on. Based on a known weight for each denomination, the separate amounts are able to be calculated as well as the total amount.

In some embodiments the device 100 includes security features. Any one or more features are able to be included such as data being encrypted on the device 100, data being encrypted when it is sent over a network, password use, firewall use and/or other security measures. In some embodiments, the data is protected sufficiently to meet or exceed Health Insurance Portability and Accountability Act (HIPPA) standards and/or other standards.

In some embodiments, the methods, aspects of the methods and components of the device 100 described herein are implemented in software, hardware, firmware or any combination thereof. For example, the methods or aspects of the methods are able to be implemented as applications for an iPhone or similar device.

An example of using the device 100 is for birth control to remind a woman to take a pill at a specified time each day. The device 100 is also able to monitor whether a woman has taken a pill on time. Another example of using the device 100 is to monitor contact lens usage. Since users do not always wear their contact lenses every day, they will have to guess when it is time to replace the contact lenses, and the contact lens seller will not know when to send replacement lenses. By monitoring the number of times the user removes the contact lenses from the device 100 and knowing how many times contact lenses are able to be worn before they should be replaced, the device 100 is able to notify the user and/or the seller to replace the lenses, for example, after x uses, the seller is able to send or offer to send additional/replacement lenses. Another example of using the device 100 is to monitor children's vitamins. Since children do not necessarily remember taking vitamins, the device 100 is able to ensure that a child took his daily vitamin by keeping a log of whether or not a vitamin was taken on a daily basis. Baby food (including the container) is able to be weighed to monitor a baby's intake. Similarly, a baby bottle and formula or breast milk are able to be weighed.

In another example, the timing/amount of feminine hygiene products (e.g. pads, tampax) is monitored. A woman's ovulation time is able to be calculated based on the use to inform a user when or when not to have sex. For example, according to some sources, the gender of a child is able to be affected by the time period of ovulation the individuals have sex. Thus, the device 100 is able to help guide in having sex at the appropriate time for a desired gender. Similarly, birth control is able to be monitored.

In some embodiments, item usage information and/or other information obtained on the device 100 is communicated to advertisers, stores, data collection agencies and/or other similar entities. These entities are able to process the information for medical studies, economic benefits or for other purposes. For example, if an advertiser knows a user is about to run out of milk, the advertiser is able to send an advertisement and/or coupon for milk. Similarly, if an advertiser knows a user just purchased bagels, the advertiser is able to provide a coupon for cream cheese. Viral marketing techniques are able to be used as well. For medical studies, the device 100 is able to facilitate tracking of user progress and conditions as well as provide other assistance to the study.

FIG. 2 illustrates a block diagram of a device 100 according to some embodiments. The device 100 includes a weighing component 102, a data processing component 104 and an I/O component 106. The weighing component 102 is able to be/include a scale 200. The data processing component 104 is able to be/include a processor 220, a memory 222, a storage 224, a computer system 226 and/or one or more databases 228. The I/O component 106 is able to be/include a keyboard 250, touchpad 252, mouse 254, barcode reader 256, RFID reader 258, display 260 such as an LCD display, image acquisition 262, screen/monitor 264 such as a touchscreen, computer 266, dial(s)/lever(s)/knob(s)/button(s) 268, voice recognition 270, a wireless component 272, wi-fi 274, networking capabilities 276, blood pressure monitor 278, insulin monitor 280, thermometer 282, alert/alarm mechanism 284, a GPS 286, a speaker 288, a radio 290, a television 292, security features 294 and one or more indicators 296 such as LEDs. The storage 224 is able to be any storage including but not limited to an internal or an external hard drive, a DVD, a CD, a flash memory, a network-attached storage and/or any other storage. Components such as the barcode reader 256 and the RFID reader 258 are able to read information from an RFID tag or a barcode such as medication information. The device 100 is able to include any of the components shown in addition to other components as well. Any input components are able to be included. Any output components are able to be included. Any other devices that are able to couple to/communicate with/be a part of the device 100 are able to be included.

FIG. 3 illustrates a flowchart of a method of using the device according to some embodiments. In the step 300, information about an item is received by the device. In some embodiments, the information is input by a user, acquired by the device, scanned in, sent to the device over a network or any other implementation so that the device is able to identify the item. For example, a user enters a name of the medication (e.g Lipitor) and the number of pills via a keyboard. In another example, the information is scanned using an RFID reader.

In the step 302, a schedule for using or reminding a user about the item (e.g. taking a medication) is configured. Scheduling is able to be performed by a user inputting in a schedule, the I/O component reading the schedule (e.g. RFID scanner scans in schedule), the schedule is able to be received over a network from a pharmacy or doctor or any other means of scheduling is possible.

In some embodiments, scheduling is able to be skipped. In some embodiments, a default time is used to remind users (e.g. at 8 pm or for multiple times—8 am and 8 pm). In some embodiments, instead of using a schedule, a calculated time is used for reminding a user. For example, the device calculates the reminding time. The reminding time is able to be calculated based any one or more factors such as the last time a medication was taken, the amount of medication taken, the weight of the user and other factors.

In the step 304, the item such as a medication is weighed on the device. The weighing is able to be done in many different ways such as weighing an individual item and then a container full of items, or weighing the container full of items, weighing an individual item, weighing the item(s) without a container, weighing only the container, weighing a partially full container after medication is taken/computing weight/storing data and/or any other way. In some embodiments, the initial weighing is able to be skipped if the weight information is already known, for example if a combined container and medication weight, the container weight, total medication weight, individual medication weight, or other weight is known and/or able to be input or received.

In some embodiments, the item such as the medication and container remains on the device after a user takes some medication. Weighing is able to include calculating a weight difference. Weighing is also able to include storing the weight information, weight difference information and/or other information.

In the step 306, the device alerts/reminds a user. Alerting the user is able to be based on an improper weight detection (e.g. too many pills have been taken); based on the schedule it is time to take the medication and based on the weight detected, the pill has not been taken yet; based on a time since the medication was last taken (e.g. a time difference); and any other reason for alerting. For alerts that repeat until the medication is taken, the alert is able to be turned off manually or by taking a medication (e.g. 1 pill) and placing the container with medication on the device so that the device recognizes that the medication has been taken. A user does not have to wait for the device to remind the user before taking a medication. For example, if the reminder is scheduled to go off at 8 pm, and the user takes the medication at 7:58, the reminder will not go off that night since the medication has already been taken. Additional steps are able to be included throughout the use of the device including inputting additional information, monitoring for conflicting drug interactions, communicating with an external device, performing dietary tasks and other implementations. The steps are able to be repeated. For example, each day the device monitors a user's drug usage and informs the user when it is time to take his/her medication. The order of the steps is variable. For example, the step of scheduling is able to be first. Many other orders are possible. Additionally, in some embodiments, one or more steps are able to be skipped. In some embodiments, scheduling takes place once for an item and the schedule is stored. Then, the steps of weighing and reminding are able to be repeated so a user does not miss a medication.

FIG. 4 illustrates a flowchart of a method of using the device for dietary purposes according to some embodiments. In the step 400, an item is weighed. For example, an apple is weighed.

In the step 402, input information related to the item is selected/input. For example, an apple is selected from a list of fruits to eat. In the step 404, information is computed for the item. For example, based on knowledge in a database, the calories, protein, vitamins, fiber and other dietary information is calculated for the apple based on the weight (e.g. according to the database, an apple has 50 calories per ounce, the weighed apple is 5 ounces, so eating the apple is roughly 250 calories).

In the step 406, information is optionally displayed. For example, information such as text, a graph, a chart, a list and/or any other form of displaying information displays the dietary information related to the item and/or the day's worth of items and/or another time period's worth of items. In some embodiments, before or after any of the steps, a user is able to input a diet such as goals or a schedule. In some embodiments, before or after any of the steps, a user is able to input health conditions such as high blood pressure. In some embodiments, based on the weight of the item, the device is able to suggest the type of food. For example, if the food weighs 5 pounds, the device is able to provide a list of items that are able to weigh 5 pounds such as a watermelon as opposed to a strawberry. The order of the steps is able to be varied (e.g. the step 402 is able to occur the step 400).

EXAMPLE

On a first day, a user weighs a glass of milk and a bagel for breakfast. The user selects the items from the list. The device 100 computes dietary information based on the weight information. The device 100 then displays the dietary information. The user performs similar actions for lunch and dinner. At the end of the day, the user is able to review the foods and dietary information taken. The process is able to be repeated each day. Daily, weekly, monthly and/or yearly information is able to be maintained and tracked. Additionally, vitamin information is able to be included. This also enables a parent to monitor a child's intake. Water or liquid intake is able to be monitored as well. For example, a user is able to place a glass of water on the device 100 to be weighed, which is able to calculate how many ounces of water is drunk, so that the user is able to ensure he/she is drinking the desired number of ounces of water.

Figure 5:
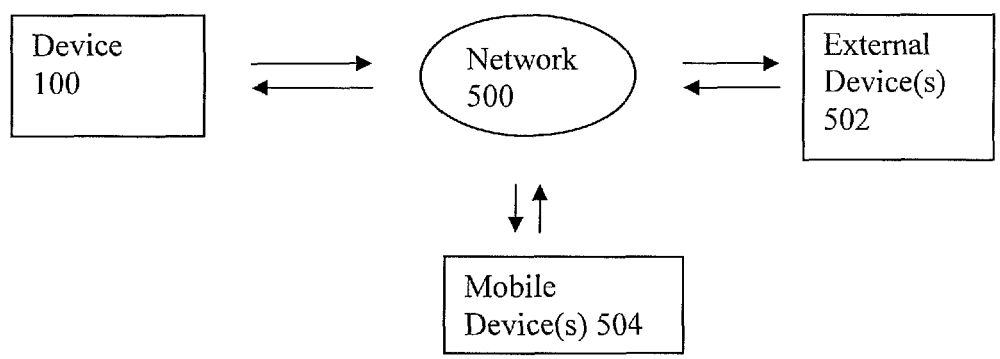
FIG. 5 illustrates a diagram of a network of devices according to some embodiments.

FIG. 5 illustrates a diagram of a network of devices according to some embodiments. The network of devices includes the device 100, a network 500 such as the Internet, and an external device 502 such as a pharmacy's computer or any other device. The network of devices is able to include additional devices as well such as a mobile device 504. The device 100 and the external device 502 are able to communicate with each other so that when a medication is nearing time for a refill, the pharmacy is able to automatically send the refill to the user in a timely manner. Similarly, other items are able to be automatically refilled or purchased. For example, the device 100 is able to couple to a store or supermarket device to automatically order vitamin refills. Additionally, the device 100 is able to automatically request and/or receive food when the user is running out of a food item. In some embodiments, the device 100 queries a user and/or enables the user to accept a refill/purchase. For example, a user typically takes a multivitamin every day but misses a few days here and there. To help the user keep track of when to refill, the device 100 monitors the usage and when the quantity is running low (e.g.

5 pills left), a refill is ordered for the user. Any item is able to be ordered/refilled manually or automatically. The mobile device 504 as described herein is able to communicate or sync with the device 100, for example, to receive alerts/reminders when the user is not near the device 100. The mobile device 504 is also able to be another user's device such as a relative.

Figures 6, 7:
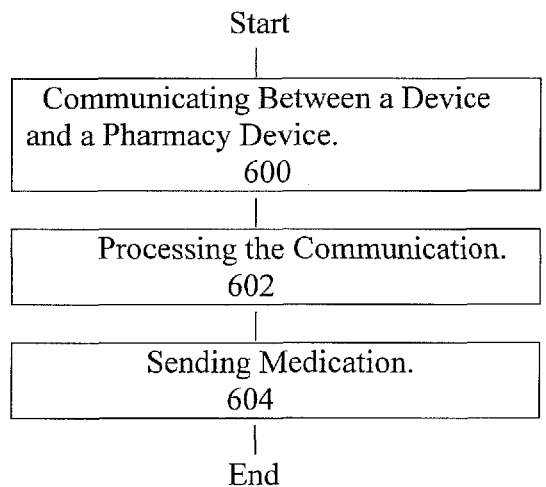
FIG. 6 illustrates a flowchart of a method of a pharmacy automatically sending a refill of a medication according to some embodiments.
FIG. 7 illustrates a database according to some embodiments.

FIG. 6 illustrates a flowchart of a method of a pharmacy automatically sending a refill to a medication according to some embodiments. In the step 600, a device communicates with a pharmacy device through a network. For example, each time there is a weight change recorded, the device communicates this data to the pharmacy device. Another example, is where the device has a threshold or similar implementation, and when the threshold is reached, the device communicates with the pharmacy device. For example, the device knows that the medication has 30 pills, and the threshold is set at 25 to ensure the pills are timely delivered. In the step 602, the pharmacy device processes the communication. Processing the communication is able to include any processing including, but not limited to, recording/storing the data communicated, calculating the remaining pills, alerting a pharmacist to prepare the medication, automatically preparing the medication, contacting the user to determine if additional medication should be sent, contacting an insurance company for billing and/or approval, contacting a physician, determining if there are generic medications, providing coupons and any other processing. Contacting the user is able to including contacting the user's medication monitoring device and/or the user's mobile device and/or any other device. In the step 604, the pharmacy device automatically sends the medication (e.g. to a user's house) or causes the medication to be sent at the appropriate time. The medication is able to be delivered to the user via any method such as U.S. Postal Service, UPS, FedEx and direct delivery. In some embodiments, the pharmacy device is interactive with the user's device. In some embodiments, instead of the pharmacy automatically sending the medication to a user's house, a regular or an automated phone call is made to the user informing him that the medication is available for pickup. Additional steps are able to be included. In some embodiments, there are manual steps involved such as a pharmacist preparing the medication.

In some embodiments, the device that communicates with the pharmacy device is the medication reminding device 100. In some embodiments, an electronic pill box communicates with the pharmacy device. For example, every time a user opens the pill box, a signal is sent to the pharmacy device. In some embodiments, a pill dispenser with a metal backing communicates with the pharmacy device. For example, when a user pushes a pill through the metal backing, a current drop is detected which sends a signal to the pharmacy device. Any device is able to communicate with the pharmacy device to ensure that the user receives or obtains his medication in a timely manner.

Similarly, in some embodiments, the device is able to link to an insurance company's device. The insurance company device is able to record medicine usage, and the insurer's medicine use record is able to be used for awarding discounts to the insured (for preventive care use).

FIG. 7 illustrates a database according to some embodiments. The database 700 is able to include one or more databases and/or separate databases. The database 700 is able to store any data in any format. The data is able to include, but is not limited to, text, images, videos, audio and others. The database is able to include links to data including, but not limited to, text, images, videos, audio and others. An example of data includes medication information including but not limited to container weight, medication weight, chemical information, medication name, quantity, dosage, conflicts and more. Another example of data includes information regarding medication taken including, but not limited to, quantity and other daily tracking information. Additional examples of data include reminder information such as when and how often; calculations and calculated information; input data; network data; contact information such as pharmacy information (network address, phone number), doctor/nurse, relatives/friends; synchronization information such as device number; nutrition information such as calories, protein, other nutrition information, pictures/videos of food, links to foods; recipes; menus; stored information regarding food eaten; diet plans, ringtones and any other relevant data. Although a database is described herein, the information is able to be stored in any structure. The database 700 is an exemplary database. More or less data/information is able to be stored in the database.

Figure 8:
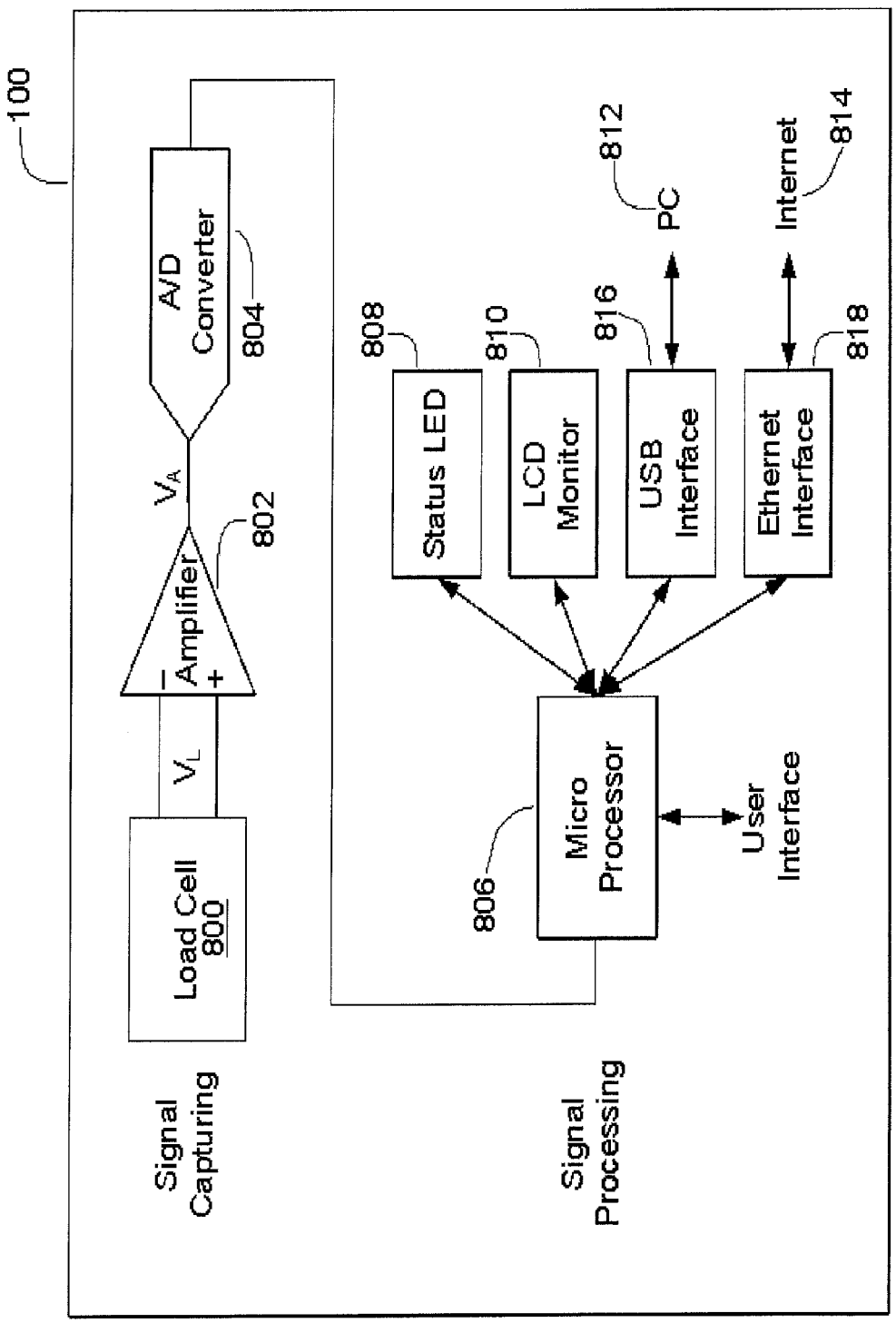
FIG. 8 illustrates hardware structures of a medication monitoring and reminding device according to some embodiments.

FIG. 8 depicts the hardware structure of the device 100 according to some embodiments. The hardware performs two main functions: signal capturing and signal processing. The signal capturing part contains a load cell 800, an amplifier 802 and an analog-to-digital (A/D) converter 804. The signal processing part includes a micro processor 806, signal lights (LEDs) 808, LCD monitor 810 and various interfaces to communicate between systems.

In some embodiments, the load cell 800 is a piezo-electric load cell and is composed of a strain gauge and a Wheatstone Bridge. When the weight on the scale changes, the shape of the strain gauge is extended and thus the resistance of the strain gauge is increased. By applying the strain gauge to a Wheatstone bridge, the change on the resistance results in a voltage change $V_L$. $V_L$ is within milli-volt range and it is hard to be detected. The differential amplifier 802, which provides a gain of several thousands, is used to amplify the $V_L$ to volt range $V_A$. To enable the signal processing, an A/D converter 804 converts the analog $V_A$ into a 14-bit digital signal.

The micro processor 806 receives the digital signal representing the weight change on the scale, takes the instruction from the user's input and then performs the corresponding signal processing. The micro processor 806 controls the light-emitting diodes (LEDs) 808 which indicate the product status and the LCD monitor 810 which provides various information to users. In addition, the product can establish communication to and from PC 812 and the Internet 814. The micro processor 806 transmits and receives data via Universal Serial Bus (USB) 816 and Ethernet interfaces 818 with proper protocols. The hardware structure described in FIG. 8 is exemplary and is not meant to limit the invention.

Figure 9:
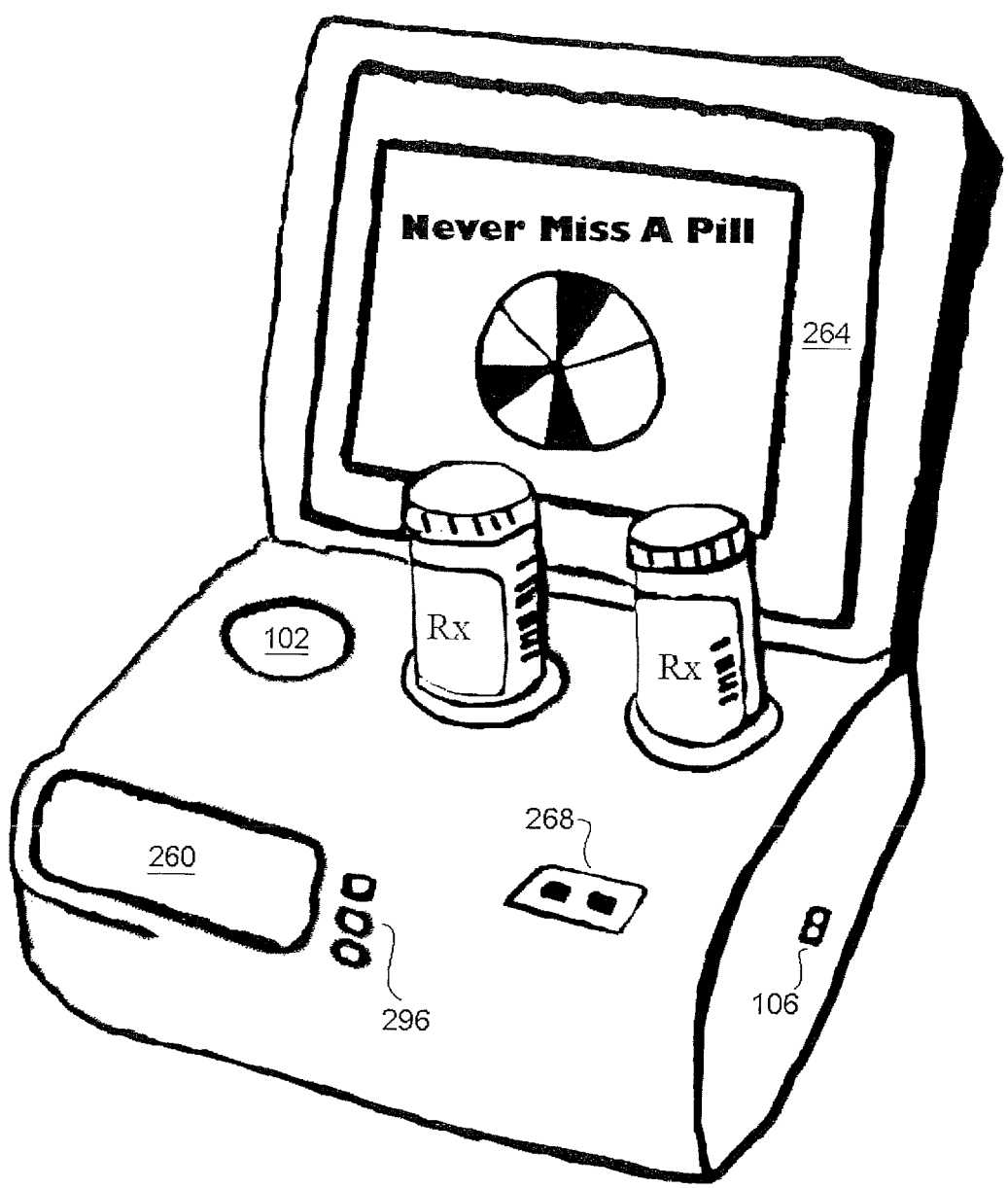
FIG. 9 illustrates an exemplary device according to some embodiments.

FIG. 9 illustrates an exemplary device 900 according to some embodiments. The exemplary device 900 includes three weighing components 102, a screen 264, an LCD display 260, LEDs 296, buttons 268 and an additional I/O component 106. The screen 264 is able to display information. The LCD 260 is also able to display information. The LEDs 296 are able to indicate status. The buttons 268 enable a user to input information. The device 900 is utilized to weigh a medication and remind a user to take the medication. Additionally, a processing component 104 (FIG. 1) is used to perform the computations described herein. The device 900 is only for exemplary purposes, and it is understood that the device 900 is able to include fewer or more components. One exemplary embodiment includes the device without the screen 264.

To utilize the medication usage monitoring and reminding device, a user places an item such as a medication on the device. The device is able to measure the item by weight. A schedule is able to be configured for notifying a user to take medications. The device then alerts a user to take the medication periodically and/or based on the schedule and is able to monitor the medication usage based on the weight. The user is able to input information to the device through many interfaces depending on the embodiment. The user is also able to retrieve information using the device.

In operation, the medication usage monitoring and reminding device provides an improved medication usage monitoring system so that a user properly and timely takes medication. The device is able to provide the monitoring by weighing the medication. The device is also able to be used for dietary monitoring and maintenance as well as communicating with pharmacies for refilling medications.

Applications:

Some applications are described herein. However, the invention is not meant to be limited to these applications in any way.

(1) In some embodiments, the device 100 is able to couple to a body-weight scale to monitor the dosage used based on user's body weight.

Current pills are designed to reach a certain concentration of an effective dosage based on either the adult or children average body weight in their respective group. However, body weight varies from one to the other. Thus, current drug design cannot be tailored based on personal needs. There is a need to customize drug taking schedule based on personal needs.

The device 100 of the Present Application is able to couple to a body-weight scale, and calculate required/optimized dosage based on user's actual body weight. In some embodiments, the device 100 is able to signal the user that it is time to take more pills or warns the user not to take another pill until certain time calculated based on user's body weight to required/suggested/desired dosage and time that last pill was taken. Similarly, based on the principle stated above, the device 100 of the Present Application is able to inform/advise the user about the appropriate dosage that should be taken based on the user's body-weight measured on the body-weight scale. For example, if a medicine is designed to have 1 pill (containing 100 mg of active ingredient) for a person with a weight of 100 pounds, when a 200 pound person takes only 1 pill, the device 100 will notify the person to take another pill to reach the suggested concentration of drugs.

(2) Similar to the principle stated in the "body-weight scale" application, the device 100 of the Present Application is able to couple to various physical and biological measurement instruments and monitor medicine use based on the actual physical response to the medicine.

Example 1

The device 100 of Present Application can couple to a heart beating rate measurement instrument. When pill x is taken, the pill x may increase the rate of heart beat. Thus, the device 100 of the Present Application can monitor the relationship between the time/amount of pill taken to the relationship of increase of heart beating rate or actual heart beating rate.

Example 2

The device 100 of the Present Application can couple to a blood analysis machine. Thus, the device can monitor the certain chemical concentration in the blood versus the time and the amount of the pill taken.

(3) The device 100 of the Present Application can couple/install MEMS (Microelectromechanical systems) or any other proper analytical instruments.

(4) The device 100 of the Present Application can couple to any recording/storage instruments. The doctors/researchers can access statistic date of certain drug usage history of particular patient, responses to a particular drug among all patients who have such device, mixing drug uses among all patients.

For example:
  (a) Patient A—take pill x on Monday, Tuesday, and Thursday in a particular week. Then the doctor can review the drug usage of patient A in particular week and the dosage of use.
  (b) 100 Patients are using pill x—10 of the 100 patients show a certain side effect to the pill x. Thus, the doctors can learn that pill x may have a likelihood of a particular side effect by collecting usage data from device 100.
  (c) Patient A take pill X, Y, Z; Patient B takes pill X, G, H, Patient C take pill Y, Z, G, H. Patient A and B both show a side effect and Patient C does not have a side effect. Thus, the data collected from device 100 of the Present Application from Patients A, B, C shows that pill X may result in certain side effect.
  (d) Patient A take pills X, Y, Z; Patient B takes pills X, G, H, Y; Patient C take pills X, Z, F; Patient D take pills Z, Y, G, F. Patient A and C die, but Patient B and D are fine. The data in the device 100 of the Present Application shows that it is likely that pill X and Z cannot be taken together.

The weighing component of the device 100 of the Present application is able to be a load cell or traditional mechanical extension/compress scale.

The device 100 of the Present Application is able to monitor the safety of the warehouse/chemical storage based on the principle described above. (i.e. by weight difference and time monitoring). Thus, the device 100 of the Present Application has security applications.

The device 100 of the Present Application is also able to use other principles to monitor the drug usage. For example, the device 100 is able to contain an image scanner. The difference between the two scans shows whether the drug has been taken or not. For example, some medicine is packed in foil seal slots having pills, and when the foil seal is broken, the pill is taken.

For example, the scanner is installed in the drawer containing medicine. The scanner is initiated to take a picture when the drawer is open. For example, at 10:00 am, the scanner routinely scans the drawer and the image taken shows no foil seal is broken, thus no pill is taken. At 1:00 pm, the drawer is opened, and the foil of one slot of is broken, which is shown on the image taken when the drawer is opened. Thus, the device 100 of the Present Application records that 1 pill is taken at 1:00 pm.

The device 100 of the Present Application is able to monitor the medicine inventory of the user and notify the medicine supplier when the inventory is low. When the amount of pills is low at the user end, the medicine supplier (pharmacy) can automatically ship the medicine to the user (patient). For example, user requires 7 pills a week and it takes 1 week for regular mail and 3 days for express mail to ship required medicine from the medicine supplier to the user. If the device 100 notifies the supplier that there are 14 pills left at the user's hand, then the medicine supplier can automatically ship the medicine to the user by regular mail. However, if the device 100 notifies the supplier that there are only 4 pills left at the user's hand, then the medicine supplier can automatically send some amount of pills to the user by express mail.

Experiment

A container of cholesterol medication contained 30 pills. Each pill weighed 10 mg.

The container and pills were weighed. Combined they weighed 800 mg.

The device computed that the container weighed 800 mg−300 mg=500 mg.

The device was set to remind a user to take a pill at 8 pm.

Later in the day, a pill was removed at 7:59 pm. When the container was placed back on the device, the combined weight was down to 790 mg, and the device recognized that 1 pill was removed. Thus, the reminder did not get triggered.

On a second day, a pill was not removed, the device recognized that a pill was not removed, and at 8 pm, the device reminded the user to take a pill. A pill was then removed from the device. When the container was placed back on the device, the device calculated that the combined weight was down to 780 mg and recognizing that another pill was taken.

The process was repeated and after the $25^{th}$ pill (the set threshold of 550 mg) was taken, the device sent a signal simulating contacting a pharmacy to send a refill.

The device is able to be any size. For example, in some embodiments, the device is travel-sized (e.g. is able fit in a pill bottle). In some embodiments, the device is tabletop-sized (e.g. a surface area of approximately 1 ft. by 1 ft).

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

We claim:

1. A device for monitoring medication usage, comprising:
   a) a medication removal recognition component configured for recognizing removal of a medication and generating medication removal recognition data;
   b) an input/output (I/O) component coupled to the medication removal recognition component, the I/O component configured for communicating I/O data;
   c) a data processing component configured for processing the medication removal recognition data and the I/O data including determining a weight change data;
   d) a medication reminding component coupled to the data processing component, the reminding component configured for reminding a user to take the medication; and
   e) an auto-refilling component coupled to the data processing component, the auto-refilling component configured for sending an auto-refilling signal.

2. The device of claim 1 wherein the medication removal recognition component is selected from the group consisting of a mechanical weighing device, an electronic weighing device, a two-sides balance and a piezoelectric load cell.

3. The device of claim 1 wherein the data processing component is configured for computing the weight change data by subtracting a non-initial weight from an initial weight to obtain a result and dividing the result by an individual medication weight.

4. The device of claim 1 wherein the data processing component is configured for computing the weight change data by subtracting a current weight from an immediately preceding weight.

5. The device of claim 1 wherein the data processing component is configured for recording at least one of a weight date, the weight change data and a time of weight change data.

6. The device of claim 5 wherein the data processing component is configured for converting at least one of the weight date, the weight change data and the time of weight change data into medication usage information.

7. The device of claim 6 wherein the medication usage information comprises at least one of a time of a medication taken, a dosage of a medication taken and a type of a medication taken.

8. The device of claim 7 wherein the I/O component comprises a display device configured for displaying the medication usage information.

9. The device of claim 6 wherein the I/O component is coupled to a second device for communicating at least one of a weight information, a stock information, a medication information and the medication usage information.

10. The device of claim 1 wherein the I/O component is coupled to a medication supply system, wherein the medication supply system is configured for receiving a notification of a quantity of the medication taken.

11. The device of claim 1 wherein the I/O component is coupled to an information system of a medical service provider, wherein the medical service provider is configured for performing at least one of monitoring, commenting, recording and replying regarding medication information received through a network.

12. The device of claim 1 wherein the I/O component is synchronized with a personal information system, wherein the personal information system provides an alert if a medication is not taken within a pre-designated time.

13. The device of claim 12 wherein the personal information system is selected from the group consisting of a mobile device, a pager, a cell phone, a blackberry, a laptop and a personal digital assistant.

14. The device of claim 1 wherein the I/O component is coupled to an information system including a medical database, wherein the medical database is configured for comparing a medication information and generating an alert if there is an incompatible medication.

15. The device of claim 1 wherein the I/O component is coupled to a physical condition monitoring device configured for monitoring a physical condition before, after, or while a medication is taken.

16. The device of claim 15 wherein the physical condition monitoring device is configured for monitoring at least one of a heart rate, a medication concentration in blood stream, a chemical fluid concentration and a physical fluid concentration in a body.

17. The device of claim 1 wherein the medication reminding component reminds a user at a computed reminder time based on a time of previous medication consumption, a medication dosage and a weight of the user.

18. The device of claim 1 wherein the I/O component is able to be selected from the group consisting of a screen/display, a keyboard, a mouse, a touchscreen, a touchpad, a light emitting diode, a speaker, a radio, a television, a computer, a dial, a lever, a knob, a button, a voice-recognition implementation, a wireless implementation, a wi-fi implementation, a network coupling, a bar code reader/scanner, an RFID reader/scanner, an image recognition component, a blood pressure monitor, an insulin monitor, a thermometer, and any combination thereof.

19. A system for monitoring medication usage implemented on a device, comprising:

a) a medication removal recognition module configured for recognizing removal of a medication and generating medication removal recognition data;
b) a data processing module configured for processing medication removal recognition data including determining a weight difference between a stored weight and a current weight for a first amount of pills to calculate an average weight of each pill of the first amount of pills and storing the weight difference;
c) a network module configured for communicating network information between the data processing component and an external device, wherein the external device comprises an information system of a medical service provider;
d) a reminding module coupled to the data processing module, the reminding module configured for reminding a user to take the medication based on a schedule; and
f) a display coupled to the data processing module, the display configured for displaying medication information.

20. A method of monitoring medication usage comprising:
a) receiving medication information at an Input/Output (I/O) component;
b) weighing a medication with a device and including computing a weight difference between a first weighing and a second weighing;
c) scheduling a schedule on the device;
d) reminding a user to take a medication based on the schedule; and
e) automatically communicating a medication refill request with an external device over a network when a specified quantity of pills is determined to have been removed, wherein the external device comprises a pharmacy device.

* * * * *